(12) United States Patent
Grez et al.

(10) Patent No.: US 9,801,691 B2
(45) Date of Patent: Oct. 31, 2017

(54) DEVICES AND METHODS FOR PROTECTING THE EYE FROM ADJACENT SKIN TREATMENTS

(71) Applicant: L'Oreal, Paris (FR)

(72) Inventors: Joseph W. Grez, North Bend, WA (US); Zane Bowman Allen Miller, Seattle, WA (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 15/404,101

(22) Filed: Jan. 11, 2017

(65) Prior Publication Data

US 2017/0119488 A1     May 4, 2017

Related U.S. Application Data

(63) Continuation of application No. 14/144,109, filed on Dec. 30, 2013.

(51) Int. Cl.
*A61B 90/00* (2016.01)
*A61M 11/00* (2006.01)
*A61N 7/00* (2006.01)

(52) U.S. Cl.
CPC .......... *A61B 90/04* (2016.02); *A61M 11/007* (2014.02); *A61N 7/00* (2013.01); *A61B 2090/049* (2016.02); *A61B 2090/0427* (2016.02); *A61B 2090/0472* (2016.02)

(58) Field of Classification Search
USPC ......................................... 604/290, 294–303
See application file for complete search history.

(56) References Cited

U.S. PATENT DOCUMENTS

| | | | |
|---|---|---|---|
| 5,754,273 A | 5/1998 | Luce | |
| 5,779,633 A | 7/1998 | Luce | |
| 7,201,732 B2 | 4/2007 | Anderson | |
| 2004/0050964 A1 | 3/2004 | Wong et al. | |
| 2008/0119913 A1* | 5/2008 | Powell | A61N 5/0616 |
| | | | 607/88 |
| 2011/0205383 A1 | 8/2011 | Shah | |
| 2013/0208167 A1 | 8/2013 | Chou et al. | |
| 2014/0343574 A1 | 11/2014 | Ignon et al. | |

FOREIGN PATENT DOCUMENTS

| | | |
|---|---|---|
| EP | 2357626 A1 | 8/2011 |
| WO | 2006005443 A2 | 1/2006 |
| WO | 2006092022 A1 | 9/2006 |

* cited by examiner

*Primary Examiner* — Jennifer Dieterle
*Assistant Examiner* — Farshad Negarestan
(74) *Attorney, Agent, or Firm* — Christensen O'Connor Johnson Kindness PLLC

(57) ABSTRACT

A skin care apparatus suitable for use in proximity to a subject's eyes. The apparatus includes a treatment device and a stimulus device. Upon activation by a user, such as the subject or a technician, a stimulus delivered by the stimulus device causes the subject's eyelid to close prior to the administration of a skin care treatment by the treatment device.

7 Claims, 2 Drawing Sheets

DEVICES AND METHODS FOR PROTECTING THE EYE FROM ADJACENT SKIN TREATMENTS

CROSS-REFERENCE TO RELATED APPLICATION

This application is a continuation of application Ser. No. 14/144,109, filed Dec. 30, 2013, the entire disclosure of which is incorporated by reference herein.

BACKGROUND

Skin surrounding the eye is commonly covered with various cosmetics such as eye liner, base coatings, coloring, etc. Such coatings must be removed periodically, and removal techniques typically involve the manual application of chemicals, usually with a cotton pad or facecloth. These cleaning chemicals are not intended for direct exposure to sensitive eye tissues and it is normal for people to close their eye-lids to prevent exposure during cosmetic cleaning around the eye.

Increasingly, the skin surrounding the eye is also a target of cosmetic treatments for conditions such as wrinkle reduction, "bags" or dark circle reduction, and other skin color and texture conditions concerning the skin adjacent the eyes. These treatments can include sprays, sonic cleansing, microdermabrasion, light, and the like. These treatments are less predictable to use than a facecloth, and therefore, could accidentally be activated while the eye is still open.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with aspects of the present disclosure, a skin care apparatus for treating an area adjacent a subject's eye is provided. The apparatus includes a body, a treatment device carried by the body, a stimulus device carried by the body, a treatment switch, and a treatment control coupled to the treatment device and the stimulus device. In some embodiments, the treatment control, when signaled by the treatment switch, is configured to cause the stimulus device to generate a stimulus and to administer the stimulus at the subject's eye suitable for closure thereof, and thereafter, is configured to cause the treatment device to administer a treatment to the area adjacent the subject's eye.

In accordance with another aspect of the present disclosure, a method is provided for treating an area adjacent a subject's eye. The method comprises administering a stimulus at the subject's eye; and thereafter administering a treatment to the area adjacent the subject's eye.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The detailed description set forth below in connection with the appended drawings where like numerals reference like elements is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

The following discussion provides examples that relate to skin care. In particular, some examples described herein are directed to skin care devices that provide techniques for forcing the eye lids of a subject to close just prior to the administration of a skin care treatment. The skin care treatments can include but are not limited to cosmetic cleaning around the eye, laser treatment, ultrasound, microdermabrasion, etc. In the examples that follow, the devices and methods employ techniques that stimulate the eye's natural blink reflex. This stimulus can be a flash of light, a puff of air, a burst of sound or pressure, though other stimulus techniques could be used.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Figure 1:
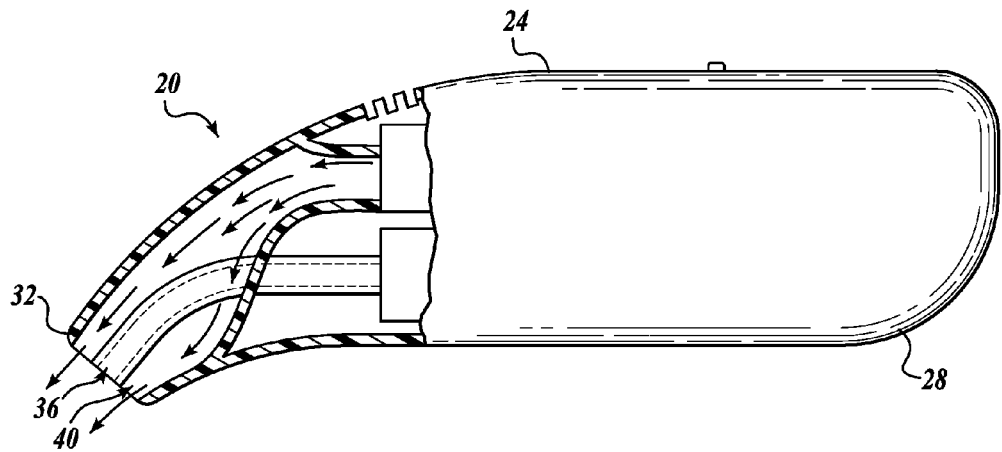
FIG. 1 is a schematic view of one example of a skin care apparatus in accordance with aspects of the present disclosure.
Figure 2:
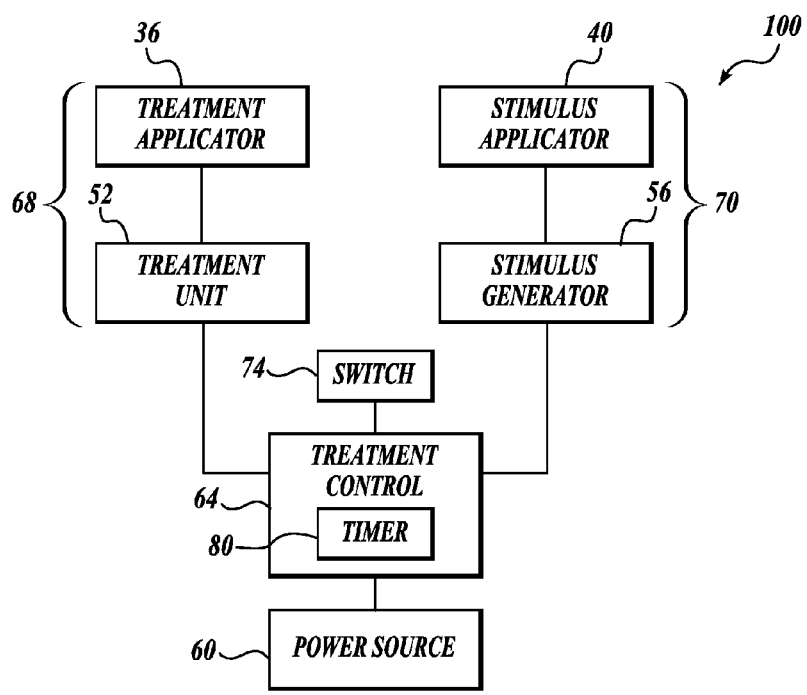
FIG. 2 is a block diagram of the skin care apparatus of FIG. 1.

Turning now to FIG. 1, there is shown one example of a skin care apparatus generally designated 20, formed in accordance with aspects of the present disclosure. The skin care apparatus 20 is suitable for use in proximity to a subject's eyes. As shown in FIGS. 1 and 2, the apparatus 20 includes an ergonomic body 24, the rearward portion of which forms a handle 28. A treatment head 32 is disposed at the forward end of the body 24. The treatment head 32 includes a treatment applicator 36 that administers a treatment to a skin region adjacent to or surrounding the subject's eye, and a stimulus applicator 40 that administers a stimulus in order to stimulate the eye's natural blink reflex. As will be described in more detail below, upon activation by a user, such as the subject or a technician, the stimulus delivered by stimulus applicator 40 causes the subject's eyelid to close prior to the administration of a skin care treatment by the treatment applicator 36. In some embodiments, the stimulus delivered by stimulus applicator 40 causes the subject's eyelid to close just prior to the initiation and/or administration of a skin care treatment by the treatment applicator 36. In these or other embodiments, the administration of the stimulus continues throughout the duration of the skin care treatment. As a result of these aforementioned embodiments, a subject's eyelids are forced close to prevent exposure during the skin care treatment.

Still referring to FIGS. 1 and 2, the body 24 houses the operating structure of the appliance. As shown in block diagrammatic form in FIG. 2, the operating structure in one embodiment includes a treatment unit 52, a stimulus generator 56, a power source 60, such as a rechargeable battery, and a treatment control 64. The treatment unit 52 in conjunction with the treatment applicator 36 forms a treatment device 68 and the stimulus generator 56 in conjunction with the stimulus applicator 40 forms a stimulus device 70. In some embodiments, a power cord coupled to the power supply supplies power via a "mains" power source.

The treatment control 64 includes an on/off button configured and arranged to selectively deliver power from the power source 60 to the treatment device 68 and the stimulus device 70. In some embodiments, the treatment control 64 may also include a treatment switch 74 coupled to control circuitry, such as a programmed microcontroller or processor, which is configured to control the administration of the stimulus by the stimulus device 70 and the skin care treatment by the treatment device 68. In some embodiments, the treatment control 64 includes a timer 80, which can be circuitry based or software based. The timer, when initiated by the treatment switch 74, assures that the administration of the stimulus precedes the administration of the treatment by a sufficient amount (e.g., approximately 80 milliseconds or greater). In other words, the timer 80, in conjunction with the treatment control 64, is programmed to, or comprises logic that, first causes administration of the stimulus to occur and then shortly thereafter, causes the administration of the skin care treatment to occur.

In some embodiments, the stimulus device 70 can administer a stimulus that includes but is not limited to a flash of light, a puff of air, a burst of sound or pressure, etc., that causes the subject's eye to close. In the embodiment shown in FIGS. 1 and 3, the stimulus device 70 administers a puff of air. The puff of air can be generated by any suitable mechanism, including a fan, a blower, a piston, a piezoelectric device, a pump, compressed gas, among others. The air can be supplied through one or more vents 94 in the body 24.

Figure 3:
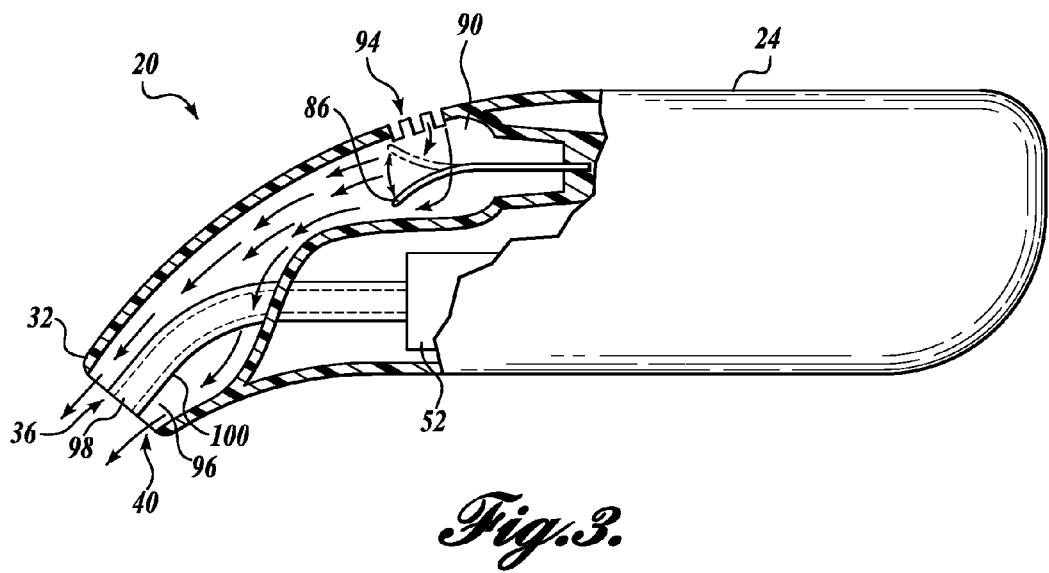
FIG. 3 is a schematic view of another example of a skin care apparatus in accordance with aspects of the present disclosure.
Figure 4:
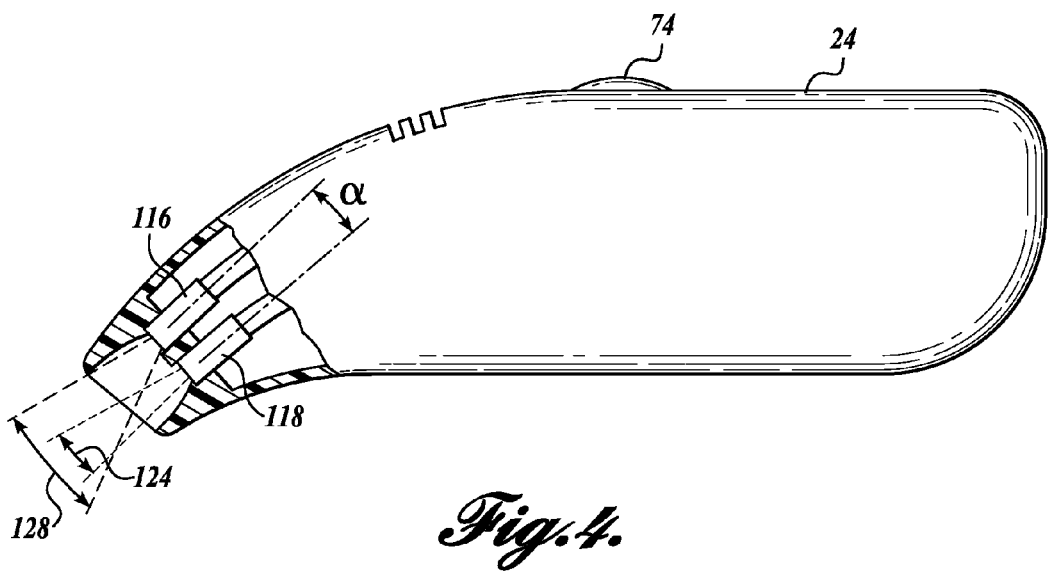
FIG. 4 is a schematic view of yet another example of a skin care apparatus in accordance with aspects of the present disclosure.

In the embodiment shown in FIG. 3, the stimulus generator 56 of the stimulus delivery device 70 includes a piezoelectric fan 86 operatively mounted in a chamber 90. A vent or other inlet/outlet 94 is positioned adjacent the fan 86 so that movement of the fan 86 draws air into the chamber 90 from exteriorly of the body 24, directs the air through the chamber 90, and discharges the air out of the stimulus applicator 40, which can include an outlet 96. In some embodiments, the fan 86 and the outlet 96 are cooperatively configured such that a minimum air velocity exiting the stimulus applicator 40 is approximately 0.4 m/s with an airflow rate of, for example, approximately 3 cc/s or greater. As shown in the embodiment of FIG. 4, the stimulus applicator 40 can include a nozzle 116.

The treatment device 68 may include any suitable components in order to carry out selected skin care treatments including but not limited to chemical, light, ultrasound, heat, magnetic or RF treatment, iontophoresis, phonophoresis, microdermabrasion, among others. In the embodiment shown in FIG. 3, the treatment device 68 administers a chemical spray. In that regard, the treatment unit 52 may include a chemical spray pump and internal fluid reservoir. In this embodiment, the chemical spray pump is connected in fluid communication with the treatment applicator 36, which can include an outlet 98, via feed conduit 100. In the embodiment shown in FIG. 4, the treatment applicator 36 can include a nozzle 118, which in some embodiments can be orientated at a relative angle α to the nozzle 116 of stimulus applicator 40 in order for the spray envelope 124 from the treatment nozzle 118 to be contained by or lie completely within the air flow envelope 128 of the stimulus nozzle 116. In some embodiments, an additional or alternative external fluid source can be coupled in communication with the spray pump.

In use, upon activation of the switch 74, the treatment control 64 operates the fan 86 so that: (1) air exits the outlet 96 at a velocity of 0.4 m/s or greater and for a duration of 80 milliseconds or longer; and (2) the skin care treatment is administered by the device 68 at least 80 milliseconds or longer after the stimulus, e.g., air, is first discharged from the outlet 96. In some embodiments, continued stimulus from the stimulus device 70 can be administered to maintain a closed-eye condition.

It should be noted that for purposes of this disclosure, terminology such as "upper," "lower," "vertical," "horizontal," "inwardly," "outwardly," "inner," "outer," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The embodiments of the invention in which an exclusive property or privilege is claimed are defined as follows:

1. A method for treating an area adjacent a subject's eye with a skin care apparatus, the skin care apparatus having a treatment switch, a stimulator, and a treatment head, the method comprising: activating the treatment switch;
   administering a puff of air at the subject's eye based on activation of the treatment switch, wherein administering the puff of air includes:
   generating the puff of air with the stimulator, and
   delivering the puff of air through the treatment head at the subject's eye to close the subject's eye via reflex; and
   after said administering the puff of air at the subject's eye, administering a treatment with the treatment head to the area adjacent the subject's eye.

2. The method of claim 1, wherein administering the treatment includes: administering a chemical treatment from an internal reservoir.

3. The method of claim 2, wherein administering the treatment includes: administering the chemical treatment with a chemical spray pump.

4. The method of claim 1, wherein the treatment is administered not earlier than 80 milliseconds after said administering the puff of air at the subject's eye.

5. The method of claim 1, wherein generating the puff of air with the stimulator includes:
   generating the puff of air from the stimulator, wherein the stimulator is selected from a group consisting of a fan, a blower, a piston, a piezoelectric fan, a pump, and a source of compressed gas.

6. The method of claim 1, wherein administering the treatment includes administering the treatment within a treatment envelope, and wherein administering the puff of air includes administering the puff of air within a stimulus envelope.

7. The method of claim 6, wherein the treatment envelope is contained within the stimulus envelope.

\* \* \* \* \*